United States Patent
Ding et al.

(10) Patent No.: US 12,028,451 B2
(45) Date of Patent: Jul. 2, 2024

(54) KEY GENERATION METHOD USING A KEY GENERATION NETWORK CONSTRUCTED ACCORDING TO A GENERATOR NETWORK AND A DISCRIMINATOR NETWORK

(71) Applicant: University of Electronic Science and Technology of China, Chengdu (CN)

(72) Inventors: Yi Ding, Chengdu (CN); Zhen Qin, Chengdu (CN); Fuyuan Tan, Chengdu (CN); Fuhu Deng, Chengdu (CN); Zhiguang Qin, Chengdu (CN)

(73) Assignee: UNIVERSITY OF ELECTRONIC SCIENCE AND TECHNOLOGY OF CHINA, Chengdu (CN)

( * ) Notice: Subject to any disclaimer, the term of this patent is extended or adjusted under 35 U.S.C. 154(b) by 493 days.

(21) Appl. No.: 17/336,339

(22) Filed: Jun. 2, 2021

(65) Prior Publication Data

US 2021/0385081 A1    Dec. 9, 2021

(30) Foreign Application Priority Data

Jun. 3, 2020    (CN) .......................... 202010495938.0

(51) Int. Cl.
| | | |
|---|---|---|
| *H04L 9/08* | (2006.01) | |
| *G06N 3/045* | (2023.01) | |
| *G06N 3/084* | (2023.01) | |
| *G16H 30/20* | (2018.01) | |

(52) U.S. Cl.
CPC ........... *H04L 9/0869* (2013.01); *G06N 3/045* (2023.01); *G06N 3/084* (2013.01); *G16H 30/20* (2018.01)

(58) Field of Classification Search
CPC ... H04L 9/0869; H04L 9/0656; H04L 9/0863; H04L 9/0891; G06N 3/045; G06N 3/084; G06N 3/0418; G06N 3/047; G06N 3/088; G16H 30/20; G16H 10/60
USPC ......................................................... 713/189
See application file for complete search history.

(56) References Cited

U.S. PATENT DOCUMENTS

| | | | | |
|---|---|---|---|---|
| 2014/0301554 A1* | 10/2014 | Cheng | ..................... | H04L 9/088 380/284 |
| 2015/0003607 A1* | 1/2015 | Choi | ..................... | H04L 63/065 380/44 |
| 2017/0346806 A1* | 11/2017 | Aissi | ..................... | H04L 63/083 |
| 2020/0117828 A1* | 4/2020 | Whitman | ............... | H04K 3/825 |

* cited by examiner

*Primary Examiner* — Bryan F Wright
(74) *Attorney, Agent, or Firm* — Bayramoglu Law Offices LLC

(57) ABSTRACT

A key generation method based on a deep learning generative adversarial network includes: preparing a training set image; construction of a key generation network: constructing the key generation network according to a generator network and a discriminator network, and inputting the training set image to the key generation network; and training of the key generation network: training the key generation network by a deep learning method to generate a key.

9 Claims, 2 Drawing Sheets

KEY GENERATION METHOD USING A KEY GENERATION NETWORK CONSTRUCTED ACCORDING TO A GENERATOR NETWORK AND A DISCRIMINATOR NETWORK

CROSS REFERENCE TO THE RELATED APPLICATIONS

This application is based upon and claims priority to Chinese Patent Application No. 202010495938.0, filed on Jun. 3, 2020, the entire contents of which are incorporated herein by reference.

TECHNICAL FIELD

The present invention belongs to the technical field of communications, and in particular, to a key generation method based on a deep learning generative adversarial network.

BACKGROUND

According to different ways of plaintext encryption, cryptosystems can be classified into block ciphers and stream ciphers. Traditional methods for block cipher encryption, such as the data encryption standard (DES), the international data encryption algorithm (IDEA) and the advanced encryption standard (AES) have been widely used in image encryption. Compared with block ciphers, stream ciphers have advantages such as high security, fast encryption and decryption speed, small error expansion, easy synchronization, and low implementation cost. The core problem of stream ciphers is the design of stream cipher generators. The strength of stream ciphers depends completely on the randomness and unpredictability of the sequence generated by the stream cipher generator. At present, common stream cipher generators capable of generating key stream sequences with good characteristics include the following: linear feedback shift registers (LFSRs), non-linear feedback shift registers (NLFSRs), finite automatons, linear congruential generators (LCGs) and chaotic systems. Among them, the chaotic systems have distinctive characteristics such as pseudo-randomness, ergodicity, periodicity, and extremely high sensitivity to initial conditions and control coefficients, attracting many researchers to use chaotic systems to generate key sequences for image encryption. In these methods, all the key generators are designed manually. In order to obtain good encryption performance, the manual design process is difficult and time-consuming, as it not only requires professional information security knowledge, but also requires prior knowledge of mathematical theory. Moreover, during the design of a key generator, it is necessary to first determine the encryption performance to be achieved, and then independently design and evaluate the key generator to judge whether the key generator can achieve the encryption performance. This is, in fact, a capricious process, not a direct process to solve the problem. Furthermore, if the encryption performance that can be achieved by using the key is known, then the key generator should be reversely designed and generated in an automatic manner by learning the expected encryption performance.

Deep learning technology is currently the most vigorous branch of the discipline of machine learning, and thus has the broadest application prospects in the field of artificial intelligence. Convolutional neural networks, as representative network structures in deep learning, have been widely used to solve computer vision tasks. Image-to-image translation is a class of vision and graphics tasks where the goal is to learn the mapping between two image domains. At present, generative adversarial network (GAN)-based methods can implement image-to-image translation more efficiently in absence of paired data. Generally, the number of parameters of a deep learning model can reach millions. During the training of a deep learning model, all weight parameters are randomly initialized, and some training strategies are adopted, such as regularization, dropout, asynchronous stochastic descent, and gradient noise amplification, making the parameters of the deep learning model extremely random. Based on this inspiration, the inventor raises a question on whether the deep learning model can be used as a key generation system to generate chaotic sequences. Additionally, a generative adversarial network for domain transfer has attracted the inventor's attention, as it can learn the mapping between two image domains to convert an image of the source domain into an image of the target domain. If the target domain is set to a desired key type, then the question arises as to whether it is possible to generate a key sequence through the generative adversarial network, where the key sequence contains the characteristics of the desired key type.

SUMMARY

In view of the above-mentioned shortcomings identified in the prior art, the present invention provides a key generation method based on a deep learning generative adversarial network. The key generated by the method has characteristics such as a larger key space, pseudo-randomness, one-time pad and sensitivity to initial values. The present invention is one of the earliest studies that attempted to adopt deep learning methods in the field of key generation. Moreover, plaintext medical images encrypted using the generated key have higher security.

In order to achieve the above-mentioned objective, the present invention adopts the following technical solution.

The technical solution provides a key generation method based on a deep learning generative adversarial network, including the following steps:

S1: preparing a training set image;

S2: construction of a key generation network: constructing the key generation network according to a generator network and a discriminator network, and inputting the training set image to the key generation network; and S3: training of the key generation network: training the key generation network by a deep learning method to generate a key.

The advantages of the present invention are as follows. In the present invention, the target domain is set to the desired key type, and a key sequence is generated through the generative adversarial network, wherein the key sequence contains the characteristics of the desired key type. The key generated by means of the present invention has characteristics such as a larger key space, pseudo-randomness, one-time pad and sensitivity to initial values. Moreover, images encrypted using the key have higher security.

Further, the generator network includes a down-sampling layer unit, a residual module layer unit, a transposed convolutional layer unit and a convolutional layer that are sequentially connected.

The down-sampling layer unit includes three down-sampling layers. The three down-sampling layers include 64 7×7 convolution kernels, 128 3×3 convolution kernels and 256 3×3 convolution kernels, respectively, and have convolution strides of 1, 2 and 2, respectively.

The residual module layer unit includes six residual module layers with identical structures.

The transposed convolutional layer unit includes two transposed convolutional layers. The two transposed convolutional layers include 128 3×3 convolution kernels and 64 3×3 convolution kernels, respectively, and have transposed convolution strides of 2 and 2, respectively.

The convolutional layer includes 3 7×7 convolution kernels, and has a convolution stride of 1.

The advantages of the above further solution are as follows. In the present invention, the generator network is used to convert an input source domain image into the style of a target domain image, and the output result is a key containing target domain attributes, thereby implementing a key generation.

Further, a loss function of the generator network is expressed as:

$$L_G = \min_G(E_{x \sim pdata(x)} \log(1 - D(G(x)));$$

wherein, $L_G$ denotes the loss function of the generator network, G denotes the generator network, D denotes the discriminator network, G(g) denotes an output result of the generator network, x denotes an input training set image of a source domain, and $E_{x \sim pdata(x)}$ denotes the distribution of a source domain training set.

The advantages of the above further solution are as follows. The generator network generates a key, and the discriminator network is used to determine whether the generated key belongs to the target domain, so that the generated key gets closer and closer to the distribution of the target domain.

Further, the discriminator network includes a first convolutional layer, a second convolutional layer, a third convolutional layer, a fourth convolutional layer and a fifth convolutional layer.

The first convolutional layer, the second convolutional layer, the third convolutional layer and the fourth convolutional layer include 64, 128, 256 and 512 4×4 convolution kernels, respectively, and each have a convolution stride of 2.

The fifth convolutional layer includes 1 4×4 convolution kernel, and has a convolution stride of 1.

The advantages of the above further solution are as follows. The discriminator network is constructed to extract features of the input image, and then a classification result is output to implement a discrimination function.

Further, a loss function of the discriminator network is expressed as:

$$L_D = \max_D(E_{y \sim pdata(y)} \log(D(y)) + E_{x \sim pdata(x)} \log(1 - D(G(x))));$$

wherein, $L_D$ denotes the loss function of the discriminator network, $E_{y \sim pdata(y)}$ denotes the distribution of the target domain training set, D(y) denotes the classification result of the discriminator network with respect to y, y denotes the input training set image of the target domain, D denotes the discriminator network, G(g) denotes the output result of the generator network, x denotes the input training set image of the source domain, and $E_{x \sim pdata}(x)$ denotes the distribution of the source domain training set.

The advantages of the above further solution are as follows. The classification function and discrimination function of the discriminator network are implemented by the loss function of the discriminator network, so that the generated key gets closer and closer to the distribution of the target domain.

Further, a loss function of the key generation network in step S2 is expressed as:

$$L = L_G + L_D;$$

wherein L denotes the loss function of the key generation network, $L_D$ denotes the loss function of the discriminator network, and $L_G$ denotes the loss function of the generator network.

The advantages of the above further solution are as follows. An adversarial relationship is established between $L_D$ and $L_G$ to make the generated key get closer and closer to the target domain.

Furthermore, step S3 includes the following steps:

S301: randomly initializing a parameter of each convolutional layer in the key generation network; and S302: updating the parameter of the key generation network by a gradient descent method to obtain an updated key generation network, and generating the key according to the updated key generation network.

The advantages of the above further solution are as follows. The parameter of the key generation network is updated to update the generated key.

Further, an expression of randomly initializing the parameter $W_n$ of each convolutional layer in the key generation network in step S301 is as follows:

$$W_n = \text{random}[w_{n,1}, w_{n,2}, \ldots, w_{n,i}];$$

wherein $w_{n,i}$ denotes an $i^{th}$ parameter of an $n^{th}$ convolutional layer of the key generation network.

The advantages of the above further solution are as follows. The network is initialized to prepare for the start of training.

Further, an expression of updating the parameter of the initialized key generation network by the gradient descent method in step S302 is as follows:

$$W_{n,i}^j = W_{n,i}^{j-1} - \alpha g \nabla J(W_n^j);$$

wherein $W_{n,i}^j$ denotes a value of the parameter $w_{n,i}$ in a $j^{th}$ training epoch, $\alpha$ denotes a learning rate, $\nabla J(W_n^j)$ denotes the gradient loss backpropagated to an $n^{th}$ convolutional layer in the $j^{th}$ training epoch, $W_n^j$ denotes all parameters of the $n^{th}$ convolutional layer in the $j^{th}$ training epoch, and J denotes the total number of training epochs.

The advantages of the above further solution are as follows. The parameter of the key generation network is updated to update the generated key.

Further, an expression of generating the key in step S302 is as follows:

$$KEY = G(W;x);$$

wherein, G(g) denotes the output result of the generator network, W contains all parameters of the key generation network, x denotes the input training set image of the source domain, and KEY denotes the key generated by the key generator.

The advantages of the above further solution are as follows. The key generated by the present invention has characteristics such as a larger key space, pseudo-randomness, one-time pad and high sensitivity.

DETAILED DESCRIPTION OF THE EMBODIMENTS

Exemplary embodiments of the present invention are described below so that those skilled in the art can understand the present invention. However, it should be clear that the present invention is not limited to the scope of the exemplary embodiments. For those ordinarily skilled in the art, as long as various changes are within the spirit and scope of the present invention defined and determined by the appended claims, these changes are obvious, and all inventions using the concept of the present invention shall fall within the scope of the present invention.

Figure 1:
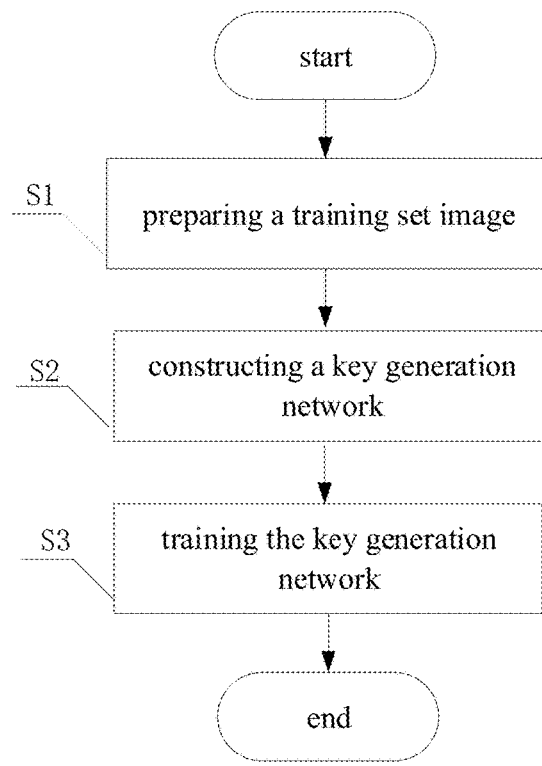
FIG. 1 is a flow chart of the method of the present invention.

Deep learning algorithms have now been widely used in the security field, but there is a lack of research on using deep learning algorithms to implement key generation. In the present invention, the generative adversarial network, as the current research focus in deep learning, is employed to implement key generation. Drawing upon the idea of image-to-image translation in deep learning in conjunction with the key generation method, the present invention proposes a key generation network based on a deep learning generative adversarial network. The key generation network has two domains: a source domain and a target domain. The source domain denotes an input image, and the input image is used as "an initial seed" to generate a private key. The target domain denotes an encryption performance to be achieved and guides a learning network to implement a private key generation process. During the training of the key generation network, a generator transmits the input image from the source domain to the target domain, the output of the generator is regarded as a key, and a discriminator is used to discriminate between the key generated by the generator and data from the target domain. The key generated by means of the present invention has characteristics such as a larger key space, pseudo-randomness, one-time pad and high sensitivity. The present invention is known as one of the earliest studies that attempted to adopt deep learning methods in the field of key generation. Moreover, plaintext medical images encrypted using the generated key have higher security. Specifically, in the present invention, the generative adversarial network is used as a key generation system. The source domain of the network can be any image. The target domain of the network is the desired key type, called the target domain herein, such as a chaotic image. The trained key generation network is capable of outputting an image that has learned the mapping from the source domain to the target domain and has the characteristics of the desired key type, that is, the key. As shown in FIG. 1, a key generation method based on a deep learning generative adversarial network includes the following steps:

S1: a training set image is prepared.

In the present embodiment, source data is acquired from 138 chest X-ray images selected from the Montgomery County X-ray dataset, and target key domain data is 138 chaotic images. The resolution of each of the training images is set as 256×256.

Figure 2:
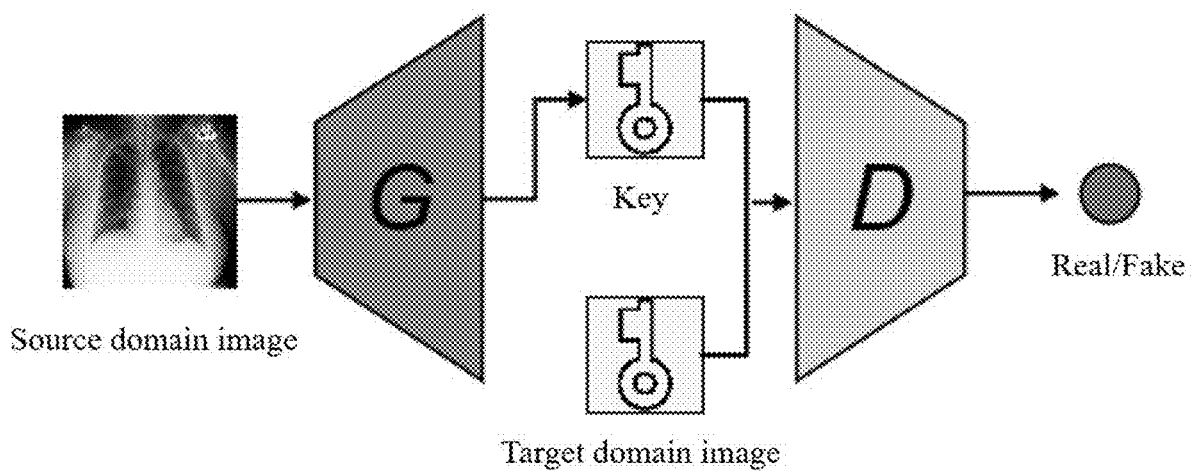
FIG. 2 is a schematic diagram of the overall architecture of a key generation network of the present invention.

S2: construction of a key generation network: the key generation network is constructed according to a generator network and a discriminator network, and the training set image is input to the key generation network;

In the present embodiment, the key generation network is composed of the generator G and the discriminator D, as shown in FIG. 2. The generator network G starts to generate a key from the source domain data and transmits the key to the discriminator. The discriminator network D is used to discriminate whether the data is from the real target domain or is fake data generated by the generator. The source data is any type of image. The target domain is a key type desired to be generated, such as a chaotic image. The trained network learns the mapping from the source domain image to the chaotic image to generate a key containing target domain attributes. In the present invention, the key generation network is trained by using a loss function, and the total loss function L is expressed as:

$$L = L_G + L_D;$$

wherein L denotes the loss function of the key generation network, $L_D$ denotes the loss function of the discriminator network, and $L_G$ denotes the loss function of the generator network.

Figure 3:
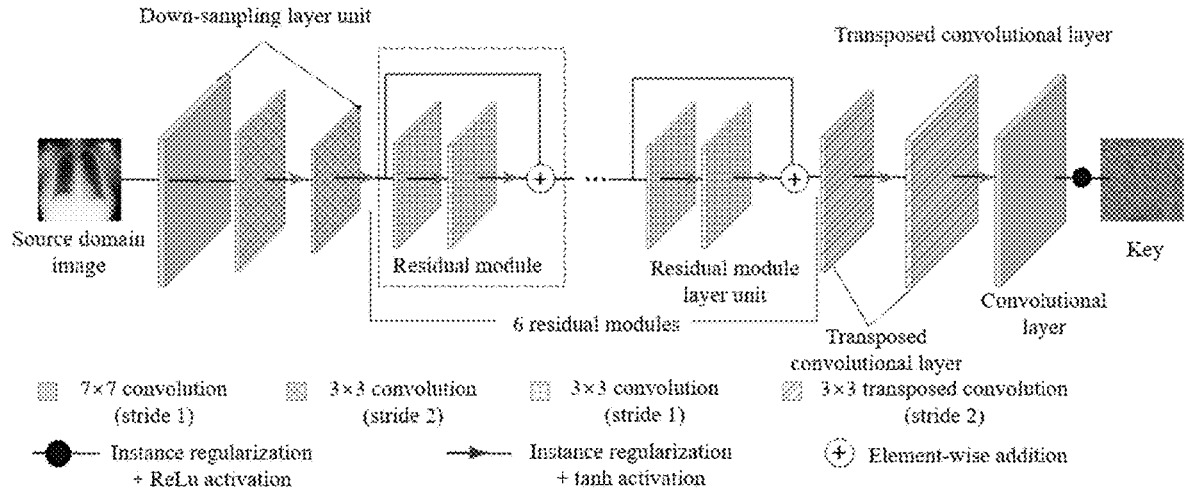
FIG. 3 is a structural diagram of a generator of the key generation network of the present invention.

The generator network G is mainly used to convert the input image from the source domain dataset into the style of the target domain image, and the output result is a key containing the target domain attributes, as shown in FIG. 3. The generator network G includes three down-sampling layers, six residual module layers, two transposed convolutional layers and one ordinary convolutional layer. The input image first passes through the three down-sampling layers with 64 7×7 convolution kernels, 128 3×3 convolution kernels and 256 3×3 convolution kernels, respectively, and convolution strides of 1, 2 and 2, respectively. This stage aims to extract image features to prepare for subsequent conversion. Then, the six identical residual modules are used to construct the content and diverse features. Subsequently, feature vectors of the image pass through the two transposed convolutional layers with 128 3×3 convolution kernels and 64 3×3 convolution kernels, respectively, and transposed convolution strides of 2 and 2, respectively, so as to restore to low-level features. Finally, the low-level features are converted into an image by the ordinary convolutional layer with 3 7×7 convolution kernels, and a convolution stride of 1. Each convolutional layer is followed by instance regularization to replace batch regularization so as to normalize a single image, thereby improving the quality of the generated image while accelerating model convergence and preventing gradient explosion. The loss function of the generator network G is:

$$L_G = \min_G (E_{x \sim pdata(x)} \log(1 - D(G(x)));$$

wherein, $L_G$ denotes the loss function of the generator network, G denotes the generator network, D denotes the discriminator network, G(g) denotes the output result of the generator network, x denotes the input training set image of the source domain, and $E_{x \sim pdata(x)}$ denotes the distribution of the source domain training set. The loss function can be understood as that the key generated by the generator maximally "misleads" the output result of the discriminator, fooling the discriminator to misjudge that the key generated by the generator comes from the target domain.

Figure 4:
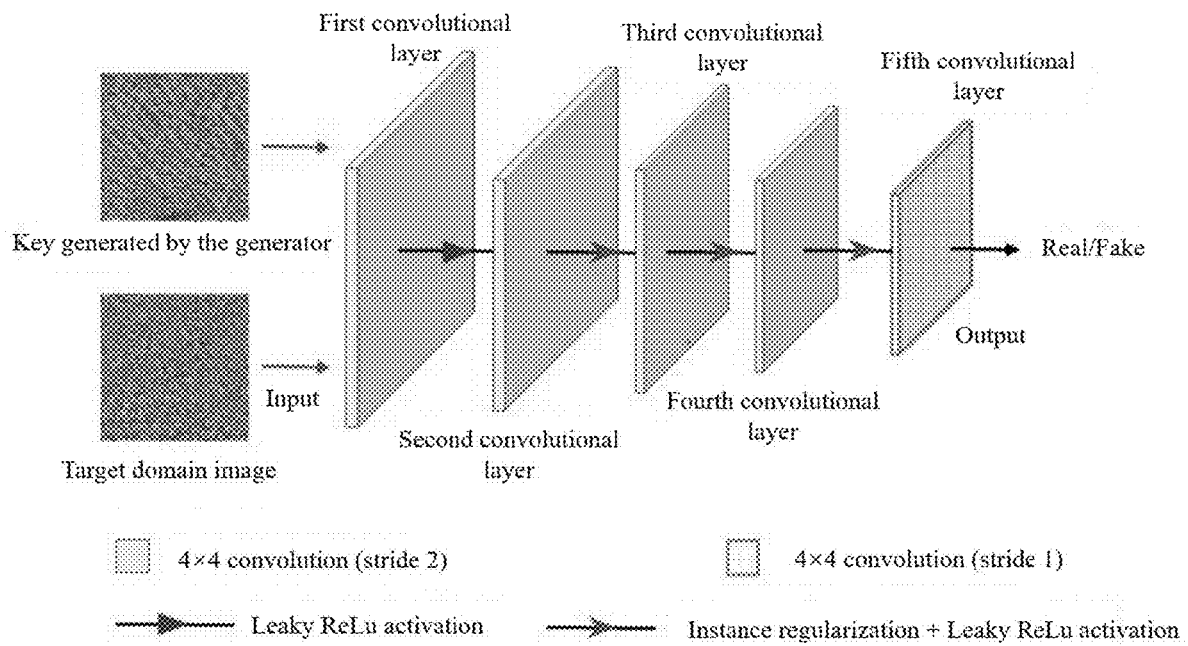
FIG. 4 is a structural diagram of a discriminator of the key generation network of the present invention.

The discriminator network D is mainly used to determine whether the output image of the generator network belongs to the target domain. As shown in FIG. 4, the discriminator network is a fully convolutional network composed of five convolutional layers. The image passes through 4 convolutional layers with 64, 128, 256 and 512 4×4 convolution kernels, respectively, and a convolution stride of 2 to extract features, and then passes through the last convolutional layer with 1 4×4 convolution kernel, and a convolution stride of 1 to generate a one-dimensional output to implement a judgment function. Excluding the last layer, the normalization is implemented by instance regularization. The loss function of the discriminator network D is expressed as:

$$L_D = \max_D(E_{y \sim pdata(y)}\log(D(y)) + E_{x \sim pdata(x)}\log(1 - D(G(x))));$$

wherein, $L_D$ denotes the loss function of the discriminator network, $E_{y \sim pdata(y)}$ denotes the distribution of the target domain training set, D(y) denotes the classification result of the discriminator network with respect to y, y denotes the input training set image of the target domain, D denotes the discriminator network, G(g) denotes the output result of the generator network, and x denotes the input training set image of the source domain.

The generative adversarial network combines the loss function of the discriminator network and the loss function of the generator network to establish an adversarial relationship. When the two networks achieve a balanced state, the probability that the discriminator network D correctly classifies the key generated by the generator network G and the chaotic image should be close to 50%. Namely, the key generated by means of the present invention is very similar to the chaotic image, so that the discriminator network D cannot discriminate between them.

S3: training of the key generation network: the key generation network is trained by a deep learning method to generate the key.

In the present embodiment, since the key generation network is a deep learning-based method, key generation in the present invention is a process of training the deep learning network. Firstly, the parameter of each convolutional layer of the key generation network is randomly initialized:

$$W_n = \text{random}[w_{n,1}, w_{n,2}, \ldots, w_{n,i}];$$

wherein w denotes an $i^{th}$ parameter of an $n^{th}$ convolutional layer of the key generation network. Thus, all the parameters W of the key generation network actually consist of all the parameters of each convolutional layer, which is defined as follows:

$$W = \text{consist}[W_1, W_2, \ldots, W_n]$$

Since the key generation network of the present invention is composed of the key generator and the key discriminator, wherein the key generator is used to generate a key, and the key generation can be expressed as:

$$KEY = G(W; x);$$

wherein, G(g) denotes a convolutional neural network of the key generator, W contains all the parameters of the key generation network, x denotes the input training set image, and KEY denotes the key generated by the key generator.

The goal of training is to make the key generated by the key generation network close to the distribution of the target domain. At the beginning of the training, the training set image is converted into feature vectors to pass through the network. This is a process of forward propagation, and this process will generate a key. In the present invention, the total loss L is calculated by using the generated key to measure the difference between the currently generated key and the target domain so as to guide the training of the network. In addition to the forward propagation, a backpropagation algorithm is also used to backpropagate the total loss to each convolutional layer, which is actually a gradient descent method. The gradient descent can be expressed as:

$$W_{n,i}^j = W_{n,i}^{j-1} - \alpha g \nabla J(W_n^j);$$

wherein $W_{n,i}^j$ denotes the value of the parameter $w_{n,i}$ in the $j^{th}$ training epoch, $\alpha$ denotes a learning rate, and $\nabla J(W_n^j)$ denotes the gradient loss backpropagated to the $n^{th}$ convolutional layer in the $j^{th}$ training epoch.

The gradient descent further updates and improves the parameters of the network, namely continuously updates and generates the key to make the key closer to the target domain. After the loss stabilizes, the key that conforms to and is close to the distribution of the target domain will be generated.

In the present embodiment, the key generation network provides the key that needs to be used by the encryption and decryption algorithms. In terms of the selection of the encryption and decryption algorithms, bitwise XOR is selected herein as the encryption and decryption methods in the experiment of the present invention. The XOR encryption and decryption algorithm is simple and easy to implement, and has a fast encryption and decryption speed. Moreover, it is proved that even with the simplest XOR encryption, the key generated by means of the present invention can provide the plaintext with higher security.

What is claimed is:

1. A key generation method based on a deep learning generative adversarial network, comprising the following steps:
   preparing a training set image;
   constructing a key generation network according to a generator network and a discriminator network, and inputting the training set image to the key generation network; and
   training a key generation network by a deep learning method to generate a key,
   wherein:
   the generator network comprises a down-sampling layer logic, a residual module layer logic, a transposed convolutional layer logic and a convolutional layer, wherein the down-sampling layer logic, the residual module layer logic, the transposed convolutional layer logic and the convolutional layer are sequentially connected;
   the down-sampling layer logic comprises three down-sampling layers with 64 7×7 convolution kernels, 128 3×3 convolution kernels and 256 3×3 convolution kernels, and convolution strides of 1, 2 and 2;
   the residual module layer logic comprises six residual module layers with identical structures;
   the transposed convolutional layer logic comprises two transposed convolutional layers with 128 3×3 convolution kernels and 64 3×3 convolution kernels, and transposed convolution strides of 2 and 2; and
   the convolutional layer comprises 3 7×7 convolution kernels, and the convolutional layer has a convolution stride of 1.

2. The key generation method of claim 1, wherein a loss function of the generator network is expressed as:

$$L_G = \min_G(ER_{x \sim pdata(x)}\log(1 - D(G(x))); \text{ and}$$

wherein, $L_G$ denotes the loss function of the generator network, G denotes the generator network, D denotes the discriminator network, G(g) denotes an output result of the generator network, x denotes an input training set image of a source domain, and $E_{x\sim pdata(x)}$ denotes a distribution of a source domain training set.

3. The key generation method of claim 1, wherein
the discriminator network comprises a first convolutional layer, a second convolutional layer, a third convolutional layer, a fourth convolutional layer and a fifth convolutional layer;
the first convolutional layer, the second convolutional layer, the third convolutional layer and the fourth convolutional layer comprise 64, 128, 256 and 512 4×4 convolution kernels, and each of the first convolutional layer, the second convolutional layer, the third convolutional layer and the fourth convolutional layer has a convolution stride of 2; and
the fifth convolutional layer comprises 1 4×4 convolution kernel, and the fifth convolutional layer has a convolution stride of 1.

4. The key generation method of claim 3, wherein
a loss function of the discriminator network is expressed as:

$$L_D = \max_D (E_{y\sim pdata(y)}\log(D(y)) + E_{x\sim pdata(x)}\log(1 - D(G(x))));$$

and
wherein, $L_D$ denotes the loss function of the discriminator network, $E_{y\sim pdata(y)}$ denotes a distribution of a target domain training set, D(y) denotes a classification result of the discriminator network with respect to y, y denotes an input training set image of a target domain, D denotes the discriminator network, G(g) denotes an output result of the generator network, denotes an input training set image of a source domain, and $E_{x\sim pdata(x)}$ denotes a distribution of a source domain training set.

5. The key generation method of claim 1, wherein
a loss function of the key generation network is expressed as:

$$L=L_G+L_D; and$$

wherein L denotes the loss function of the key generation network, $L_D$ denotes a loss function of the discriminator network, and $L_G$ denotes a loss function of the generator network.

6. The key generation method of claim 1, wherein
the training of the key generation network comprises the following steps:
randomly initializing a parameter of each convolutional layer in the key generation network; and
updating the parameter of the key generation network by a gradient descent method to obtain an updated key generation network, and generating the key according to the updated key generation network.

7. The key generation method of claim 6, wherein
an expression of randomly initializing the parameter $W_n$ of the each convolutional layer of the key generation network is as follows:

$$W_n=\text{random}[w_{n,1},w_{n,2},\ldots,w_{n,i}]; and$$

and
wherein $w_{n,i}$ denotes an $i^{th}$ parameter of an $n^{th}$ convolutional layer of the key generation network.

8. The key generation method of claim 6, wherein
an expression of updating the parameter of the key generation network by the gradient descent method is as follows:

$$W_{n,i}{}^j=W_{n,i}{}^{j-1}-\alpha g \nabla J(W_n{}^j); and$$

wherein $W_{n,i}{}^j$ denotes a value of a parameter $w_{n,i}$ in a $j^{th}$ training epoch, $\alpha$ denotes a learning rate, $\nabla J(W_n{}^j)$ denotes a gradient loss backpropagated to an $n^{th}$ convolutional layer in the $j^{th}$ training epoch, $W_n{}^j$ denotes parameters of the $n^{th}$ convolutional layer in the $j^{th}$ training epoch, and J denotes a total number of training epochs.

9. The key generation method of claim 6, wherein
an expression of generating the key is as follows:

$$KEY=G(W;x); and$$

wherein, G (g)denotes an output result of the generator network, W contains parameters of the key generation network, denotes an input training set image of a source domain, and KEY denotes the key generated by the generator network.

* * * * *